United States Patent
Naderizadeh (10) Patent No.: US 11,160,680 B2
(45) Date of Patent: Nov. 2, 2021

(54) TRACTION PROVIDER ROBOT FOR PATIENT'S FRACTURED FOOT IN SURGICAL OPERATION

(71) Applicant: Mohammad Naderizadeh, Jahroom (IR)

(72) Inventor: Mohammad Naderizadeh, Jahroom (IR)

(*) Notice: Subject to any disclaimer, the term of this patent is extended or adjusted under 35 U.S.C. 154(b) by 364 days.

(21) Appl. No.: 15/853,896

(22) Filed: Dec. 25, 2017

(65) Prior Publication Data

US 2020/0015995 A1  Jan. 16, 2020

(51) Int. Cl.
| | | |
|---|---|---|
| A61F 5/04 | (2006.01) | |
| A61F 5/042 | (2006.01) | |
| A61F 5/048 | (2006.01) | |
| A61F 5/37 | (2006.01) | |
| B25J 11/00 | (2006.01) | |
| A61B 34/00 | (2016.01) | |
| A61B 5/1455 | (2006.01) | |

(52) U.S. Cl.
CPC ........ *A61F 5/3761* (2013.01); *A61B 5/14552* (2013.01); *A61B 34/25* (2016.02); *B25J 11/008* (2013.01)

(58) Field of Classification Search
CPC .......... A61F 5/3761; A61F 5/04; A61F 5/042; A61F 5/048; A61B 34/25; A61B 5/14552; A61B 34/30; A61B 34/37; B25J 11/008; A61H 1/0218; A61G 7/0755; A61G 13/125; A61G 13/1245; A61G 7/1046; A47C 20/021; A47C 20/022
USPC ............ 5/624, 628, 86.1; 602/33, 36, 38–39
See application file for complete search history.

(56) References Cited

U.S. PATENT DOCUMENTS

| | | | | |
|---|---|---|---|---|
| 2,910,061 A * | 10/1959 | Rabjohn | ............... | A61H 1/0218 602/33 |
| 5,094,228 A * | 3/1992 | Reinert | .................. | A61H 1/008 606/243 |
| 5,645,079 A * | 7/1997 | Zahiri | ................... | A61F 5/3769 128/882 |
| 6,152,950 A * | 11/2000 | Shealy | ................. | A61H 1/0222 606/241 |
| 7,246,390 B2* | 7/2007 | Mitsuishi | ............. | A61H 1/0237 5/621 |
| 8,572,781 B2* | 11/2013 | Schlanger | ............. | A61F 5/3761 5/648 |
| 9,949,861 B2* | 4/2018 | Kreuzer | ............... | A61H 1/0218 |

* cited by examiner

*Primary Examiner* — Ophelia A Hawthorne
*Assistant Examiner* — Camtu T Nguyen
(74) *Attorney, Agent, or Firm* — Azadeh Saidi (57) ABSTRACT

The invented robot provides necessary traction for reduction of foot bone fracture in surgical operation. This robot is equipped with four electrical motor and with aid of three linear and one rotational degree of freedom assists surgery team to align broken foot bone fragments in line precisely. Hence patient foot restores its desired direction during all different stages of operation with proper traction.

9 Claims, 8 Drawing Sheets

TRACTION PROVIDER ROBOT FOR PATIENT'S FRACTURED FOOT IN SURGICAL OPERATION

FIELD OF THE INVENTION

This invention categorized as operating room equipment. Specifically the robot is invented to provide traction for reduction of patient fractured foot in operating room.

BACKGROUND OF THE INVENTION

Displacement of bones due to muscle spasms nearby fractured bones of patient with broken foot makes fixation of the bone in their desired position difficult during operation, consequently. Despite relative relaxation of muscles in surgeries with general or local anesthesia, traction of bones for reduction will be necessary because of inadequacy of muscle relaxation. This traction is applied to align broken foot bone fragments in line precisely until completeness of bone. To this end, various methods have been utilized during the ages.

The most traditional method is to apply force by operating room staffs. In this method the operating room technicians pull patient foot by hand and their weight force which is harmful for their vertebral column and wrist. Furthermore as traction period lasts long, effective and monotone traction force will be abated because of technicians' fatigue. Locating pin in the heel of patient foot and hanging weights on pin is another procedure. This method sustains damages to patient's foot and bone and causes undesired postoperative complications. To prevent foresaid problems, fracture table is utilized.

The patient foot is fixed manually on these tables which have different shapes and forms among shortcomings of such tables; taking up too much occupation space, heavy weight, and consequent transportation difficulties, limitations for widespread use in all type of fractures, time consuming installation procedure on operating table, restricted capability to connect to special tables (not all operating tables) and disability to apply traction in all directions, are mentionable. It's noteworthy that efficiency of these methods is diminished when using for larger bones like femur.

SUMMARY OF THE INVENTION

The invented robot solves aforesaid problems so causes fracture reduction with a better quality by inserting more effective and monotone traction in desired directions during surgical operation, thus facilitate the performance of surgical team.

This portable robot possesses a section for locating patient foot and provides three liner & one rotational degrees of freedom for restoring foot in desirable position by its four electrical motors. Therefore the operator adjusts position of patient foot precisely under his/her control using a display monitor or a remote control device and locating the foot in a desirable position leads to necessary traction in several directions continuously and effectively. Liner and rotational accuracy of movements of this robot are measured one millimeter and one degree respectively. Moreover oxygen content of patient blood can be shown together with foot position by the monitor.

This robot is independent with regard to the type of operating table and can be combined with any of them. Other advantages of this invention in comparison with traditional methods are as follows. Taking up less occupation space, preventing damage to foot nerves, using chargeable batteries, possible utilizing for both feet (even for massive patient) and majority of foot bones (even large size one like femur), preventing time wasting, deducting number of operating room's staffs and eliminating probable body injuries of them. Its noteworthy that place of patient foot in this robot is washable, so bacterial contaminations are kept minimized when using the invention.

DETAILED DESCRIPTION OF THE INVENTION

Figure 1:
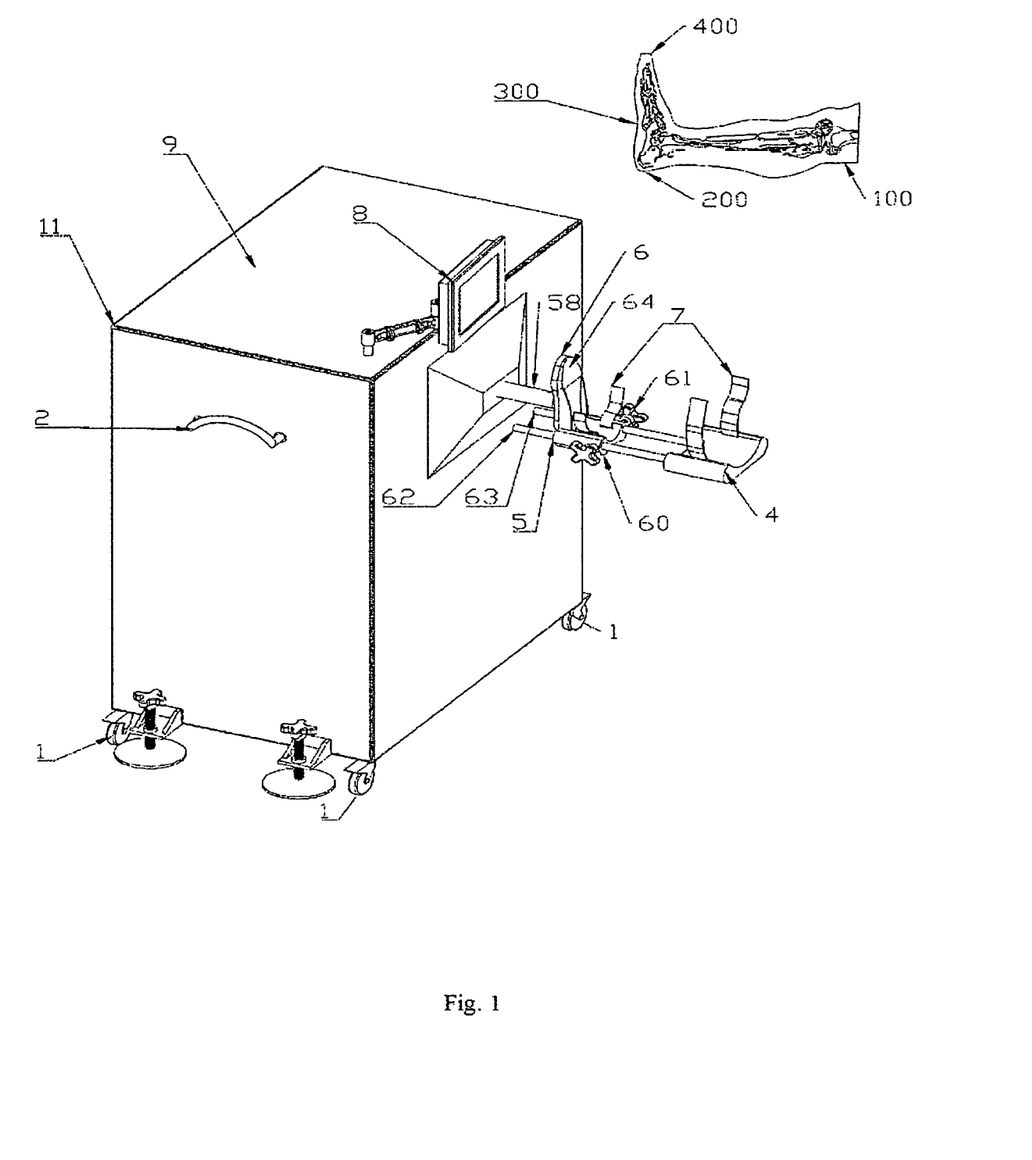
FIG. 1 shows invented robot in three-dimensional forms.

FIG. 1 shows three-dimensional view of invented robot (70). It can be carried to subjected place nearby operating table by its four wheels with lock (1) and handle (2) and is fixed on the ground by its four adjustable bases (3). The robot (70) is ready to use in this situation.

To use of the robot (70), shin (100) of patient is located on section/shin holder (4) and his/her ankle (200) on section/ankle holder (5) in such a way that the sole (300) is settled on section/sole holder (6). The next step is to secure patients' foot toward the robot (70) by ankle and shank fixator straps (7). The operator commands the robot (70) to arrange its proper situation for applying necessary traction to patient's foot by application of a finger touch screen (8) (or a remote control) which is located on top portion of case (9). By touch screen (8) all three linear and one rotational degrees of freedom for displacement of patient's foot is controllable. The desired traction is provided by the robot (70) during all different stages of the operation.

Figure 2:
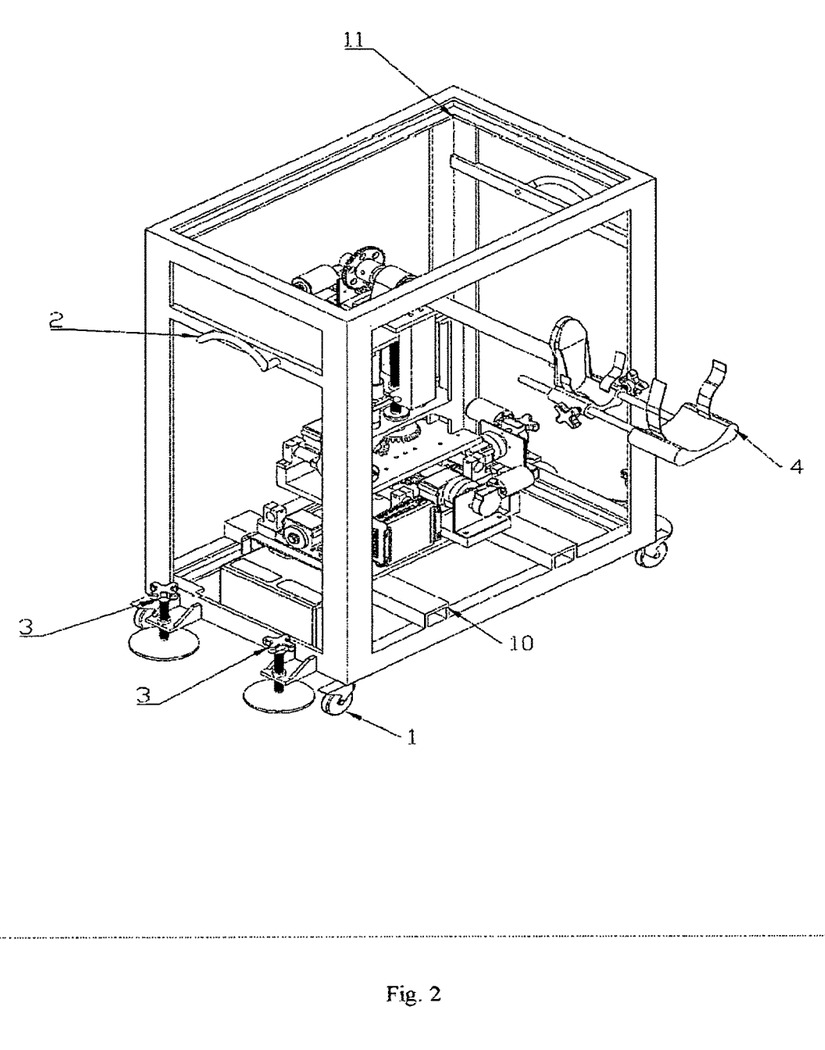
FIG. 2 shows components of invented robot in three-dimensional forms.

In FIG. 2, internal components of robot (70) can be seen when the main case ((9) in FIG. 1) is eliminated. According to this figure, two chassis (10) are installed on main body (11) of robot (70), where the movement mechanisms are erected.

Figure 3:
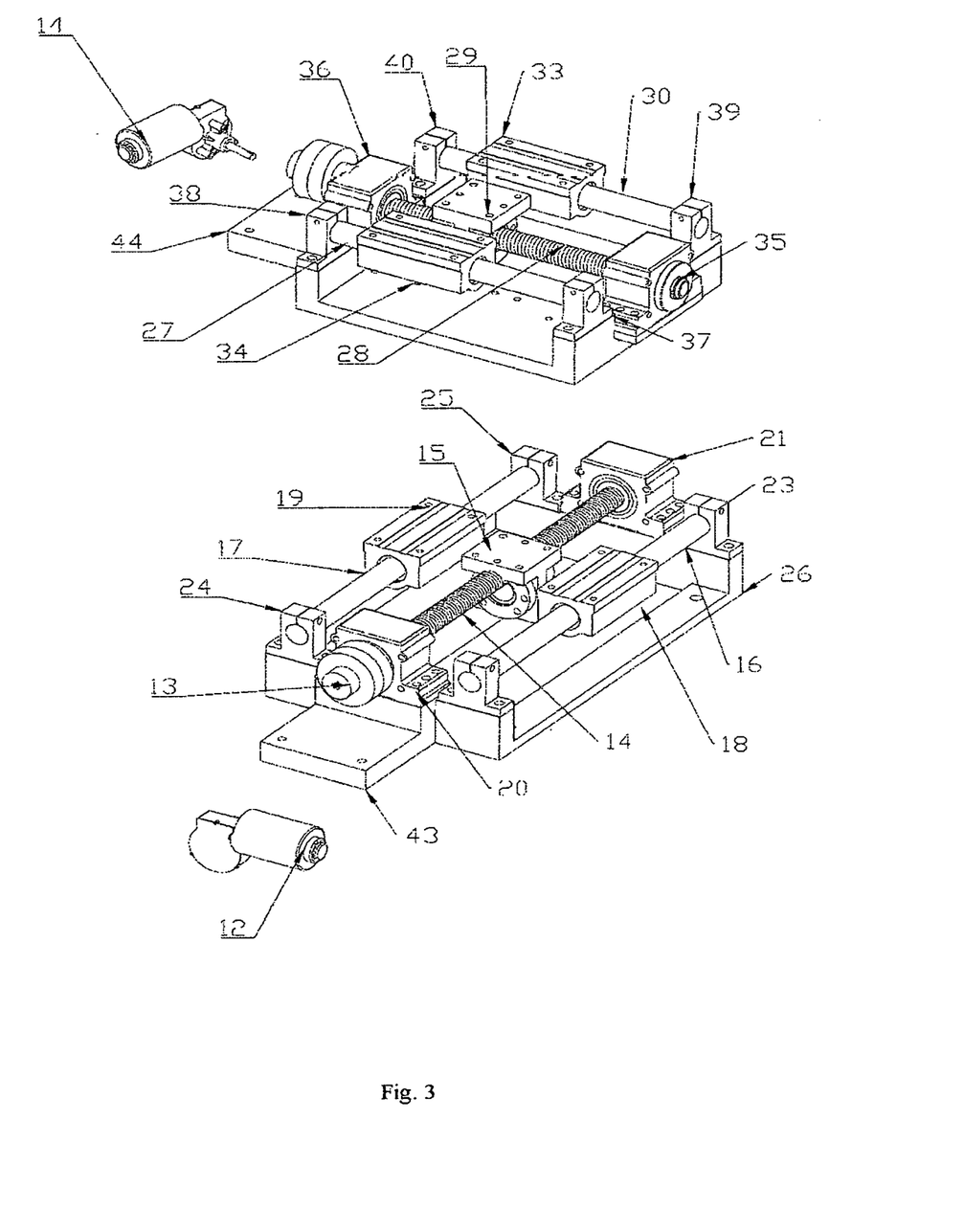
FIG. 3 illustrates components of movement mechanism of invented robot for displacement on a horizontal plate.

FIG. 3 illustrates components of movement mechanism of invented robot (70) in X and Y-axis directions. To make movement in Y-axis direction a motor-gearbox set (12) is coupled to section (13). A known mechanism named ball-screw is used to convert rotational movement of motor-gearbox set (12) to a linear displacement. The main components of this mechanism including, screw (14), nut and flange (15) are seen in FIG. 3.

As motor-gearbox set (12) is coupled to section (13), the screw (14) in ball-screw mechanism turns and nut and flange (15) moves in Y-axis direction. Linear guides/shafts (16) and (17) and wagons (18) and (19) are utilized to maintain more stability for the movement. The screw (14) by bearings (20) and (21) and linear guides (16) and (17) by stands (22), (23), (24) and (25) are joined to case (26). The lower part of case (26) is also connected to main chassis (10) of robot (70 in FIG. 2). Furthermore, the lower part of case (27) is installed on upper portion of wagons (18) and (19) and flange (15).

In FIG. 2, internal components of robot (70) can be seen when the main case ((9) in FIG. 1) is eliminated. According to this figure, two chassis (10) are installed on main body (11) of robot (70), where the movement mechanisms are erected.

FIG. 3 illustrates components of movement mechanism of invented robot (70) in X and Y-axis directions. To make movement in Y-axis direction a motor-gearbox set (12) is coupled to section (13). A known mechanism named ball-screw is used to convert rotational movement of motor-gearbox set (12) to a linear displacement. The main components of this mechanism including, screw (14), nut and flange (15) are seen in FIG. 3.

As motor-gearbox set (12) is coupled to section (13), the screw (14) in hall-screw mechanism turns and nut and flange (15) moves in Y-axis direction. Linear guides (16) and (17) and wagons (18) and (19) are utilized to maintain more stability for the movement. The screw (14) by bearings (20) and (21) and linear guides (16) and (17) by stands (22), (23), (24) and (25) are joined to case (26). The lower part of case (26) is also connected to main chassis of robot (70) ((10) in FIG. 2). Furthermore, the lower part of case (27) is installed on upper portion of wagons (18) and (19) and flange (15). Therefore, when motor-gearbox (12) turns, the case (27) will move linearly in direction of Y-axis. The case (27) can move in a 400 millimeters course.

For movement in X-axis direction, a ball-screw mechanism similar to one for Y-axis movement is considered that consists of screw (28), nut and flange (29), linear guides (30) and (31), wagons (33) and (34), bearings (35) and (36) and stands (37), (38), (39), and (40). Motor-gearbox set (41) also causes screw (28) to rotate with a same coupling as motor (12). Rotation of screw (28) causes movement of nut and flange (29) linearly in X-axis direction. Moreover, top portions of flange (29) and wagons (33) and (34) are joined to lower part of section (42) in FIG. 4, so this section ((42) in FIG. 4) moves in X-axis direction with a 300 millimeters course. Parts (43) and (44) of cases (26) and (27) are considered to locate motor-gearbox sets (12) and (41) on cases (26) and (27).

Figure 4:
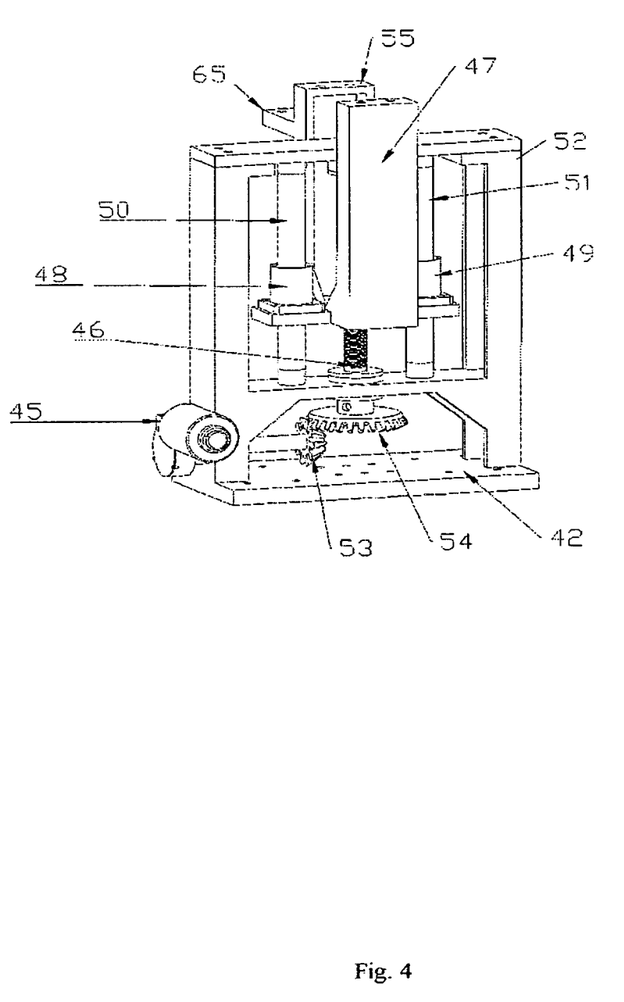
FIG. 4 shows mechanism of vertical movement of invented robot.

FIG. 4 shows components of movement mechanism of invented robot (70) in Z-axis direction (vertical) to convert rotational movement of motor-gearbox (45) to linear displacement in z direction; also, a ball screw mechanism with screw (46) has been utilized. The nut of this mechanism is installed inside an elevator (47). The wagons (48) and (49), as can be seen in FIG. 4, are connected to elevator (47) and are mounted on guides (50) and (51).

These guides and wagons are used to maintain stability. Guides (50) and (51) are joined to case (52) and screw (46) has been passed through this case. As can be seen in FIG. 4, the case (52) and elevator (47) are designed in such a way that possesses minimum volume and weight. To gain this aim, motor (45) is installed beside case (52) and two bevel gears (53) and (54) are used for power transmission to desired direction. Furthermore sections (55) in elevator (47) are connected to lower part of plate ((56) in FIG. 5). It's noteworthy that motor-gearbox (45) is controlled in such a way that patient's foot is displaced between 600 to 1100 millimeters vertically.

Figure 5:
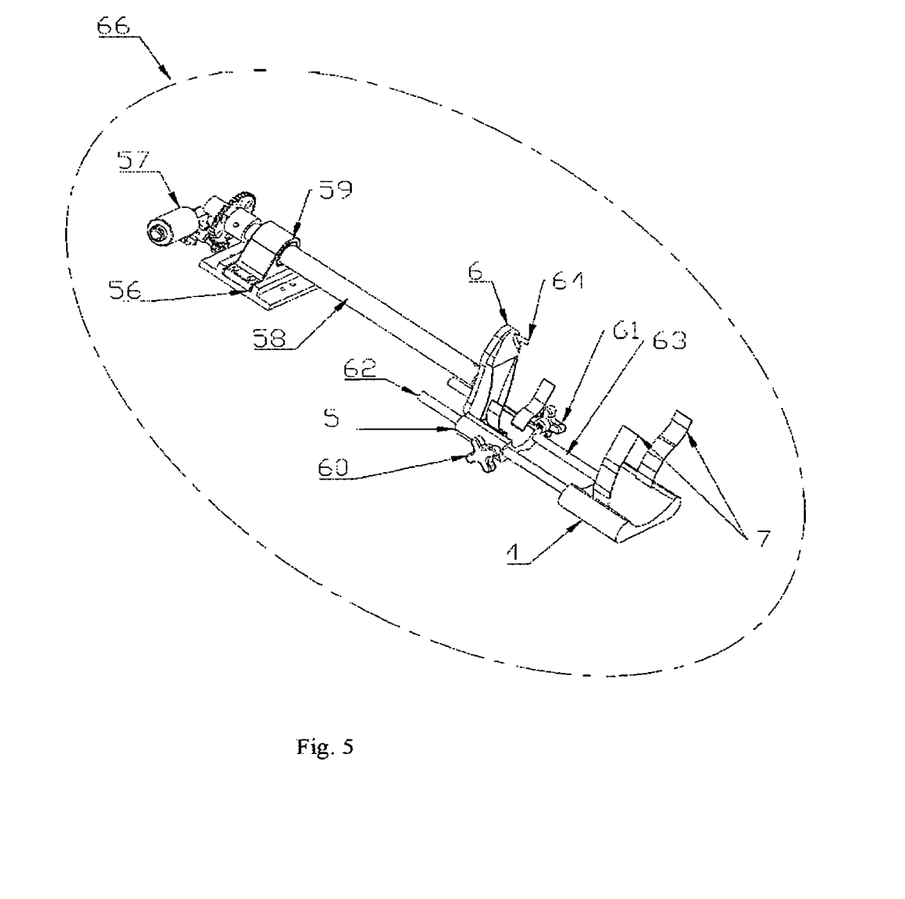
FIG. 5 presents mechanism of rotational movement of invented robot.

According to FIG. 5, motor-gearbox set (57) is coupled to shaft (58) which the other side of the shall is joined to section (6) where patient sole is located. Therefore, shaft (58) will turns when motor-gearbox set (57) rotates inside bearing (59) and patient turn in XZ-plane direction, consequently. The motor-gearbox (57) is controlled in such a way that patient foot turns in the range of −90 up to +90 in comparison with Z-axes. The bearing (59) is also mounted on plate (56).

It must be mentioned that with respect to size of patient's foot, interval between sections (5) and (4) is adjusted by the aid of adjusting screws (60) and (61) and movement of section. (5) on rails (62) and (63). A pulse oximeter (64) is also located on robot (70) to observe oxygen content of patient blood. Toe of patient is placed inside clips of oximeter and output data will be displayed on touch screen monitor ((8) in FIG. 1). Furthermore, section 65 (in FIG. 4) of elevator (47) (in FIG. 4) is considered for locating motor-gearbox (57) on elevator (47) (in FIG. 4).

Briefly, rotation of motor-gearbox sets ((12) and (41) in FIGS. 3 and (45) in FIG. 4), causes movement of section (66) (in FIG. 5) in X, Y and Z-axis directions, respectively and rotation of motor-gearbox (57) (in FIG. 5) leads to rotation of sections where patient foot located ((4), (5) and (6) in FIG. 1). It is noteworthy that the Invented robot (70) is powered by a chargeable 12 volts battery (A2, FIG. 8) and all four motors (12, 41, 45, 57) of the invented robot (70) have encoders and are controlled via central control system (A3, FIG. 8) of the robot (70) by monitor ((8) in FIG. 1) or a remote-control device by operator (not shown).

Figure 6:
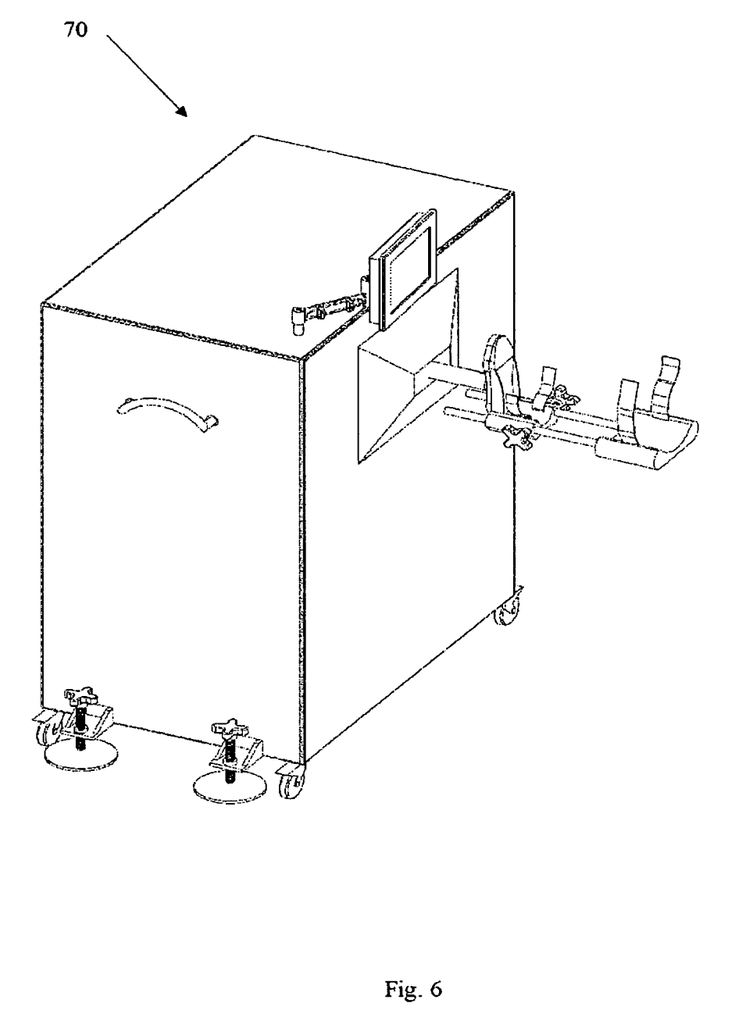
FIG. 6 displays a simplified view of the invented robot.

As displayed in FIG. 6, robot (70) is portable and can be transported the desired destination and therefore can be used in any setting or surgery site.

Figure 7:
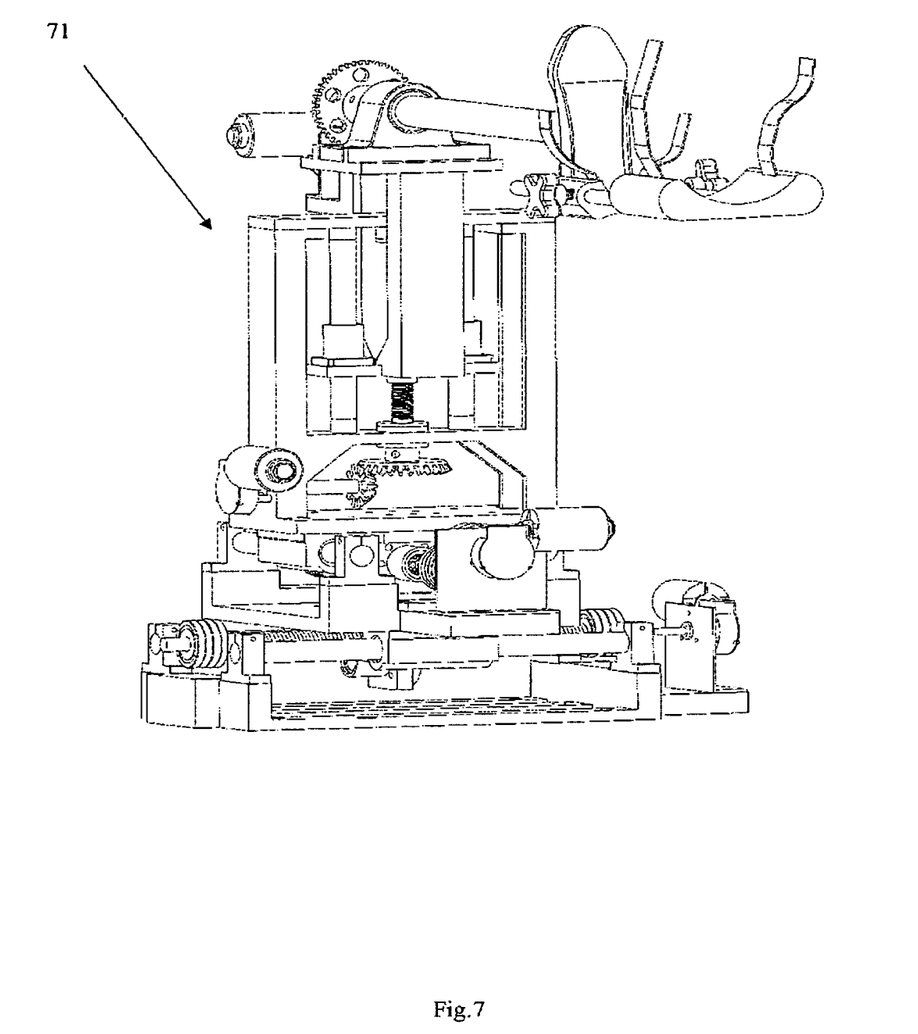
FIG. 7 displays the central control system of the robot and the wiring connections to the three-dimensional structure.
Figure 8:
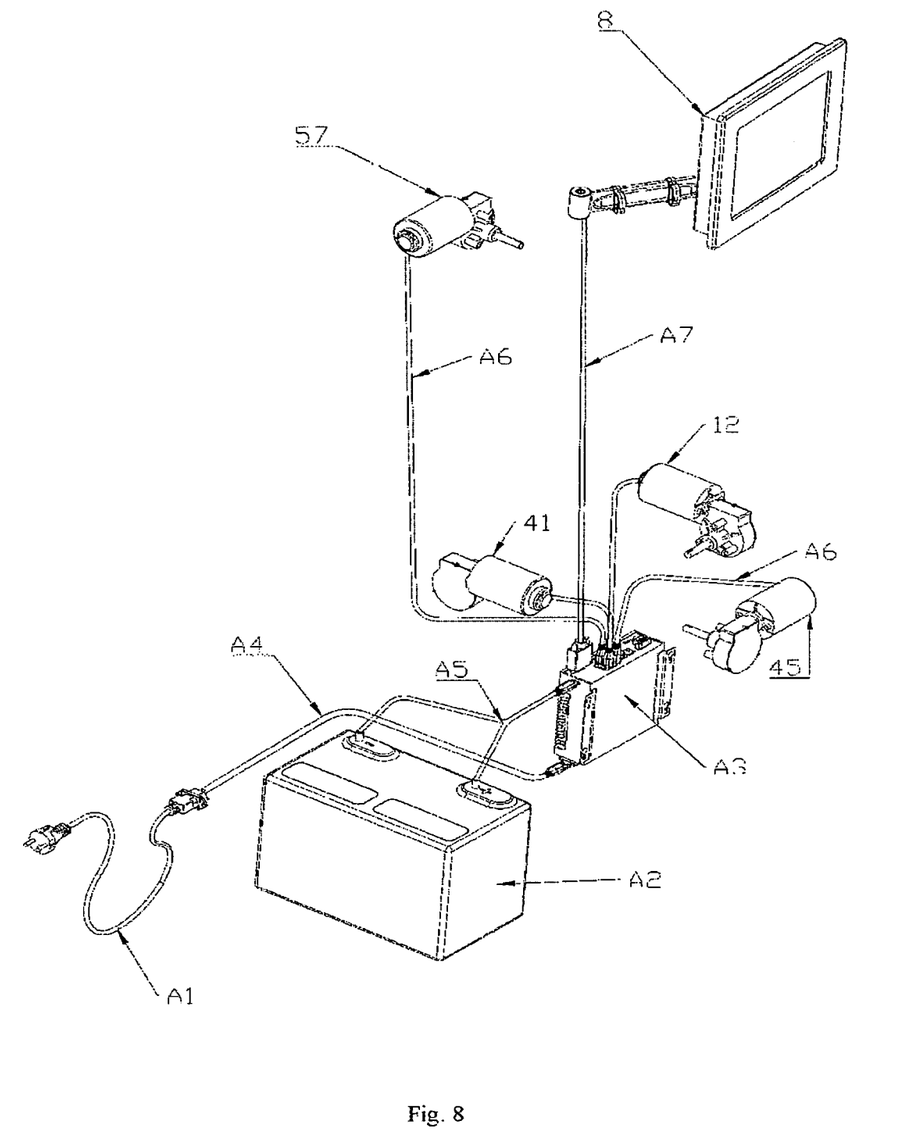
FIG. 8 displays the central control system and its connection to the monitor and other parts of the robot structure.

Robot (70) comprises different wire connection for providing power (via cables A1, A4 and A5 in FIG. 8) and communication of each one of the four motors (12, 41, 45 and 57) and the monitor (8) with the central control system (via cables A6 and A7 in FIG. 8). Wherein these connections control the three-dimensional movement of the three-dimensional moving mechanism (71, FIG. 7) as explained previously.

The invention claimed is:

1. A traction provider robot system for patient's foot in surgical operation comprising:
   a portable main body covered up by a main case;
   four wheels, and four adjustable bases, fixedly attached on either side of said main body near each one of said four wheels respectively, locking said main body and main case in place;
   an ankle holder, a shin holder and a sole holder all coupled to one another;
   multiple fixator straps, adapted to arrange and fixedly hold and displace a patient's foot accordingly;
   a central control system;
   a shaft;
   a traction provider robot is nestled inside said main case and is attached to said main body via two chassis that are fixedly attached to said main body; wherein said two chassis are perpendicular to bottom side of said main body, facing up and away from said four adjustable bases; and wherein said traction provider robot moves with a three-dimensional mechanism; wherein said three-dimensional moving mechanism is adapted to provide three linear and one rotational displacement of said patient's foot via X, Y and Z moving sections, each of the said X,Y and Z moving sections has a motor gearbox, converting rotational movements and displacement into linear displacement, wherein each of said X, Y and Z moving sections are stacked and connected to one another and are controlled separately via said central control system, wherein when one of said X, Y and Z sections is selected and programmed to move, the remaining of said X, Y and Z sections will move respectively with said selected and programmed section; and wherein said shaft is fixedly attached to said traction provider robot on one end and said sole holder on another end, transferring rotational or linear displacement of said sole holder attached to said ankle holder and shin holder to said traction provider robot and also transferring rotational and linear displacement of said traction provider robot to said ankle holder, sole holder and shin holder.

2. The robot traction provider system of claim 1, wherein said main case further comprises a touch screen display and/or a remote control device moving and controlling said traction provider robot via said central control system in any desired direction during different stages of foot operation via said X, Y and Z moving sections.

3. The robot traction provider system of claim 2, wherein said X, Y and Z moving sections each further comprising a case having at least two linear guides and at least two wagons wrapped around each one of said linear guides sliding back and forth in X and Y direction for each one of said X and Y moving sections respectively;

and moving upwards and downwards in a Z axis direction for said Z moving sections; and wherein each one of said motor gearbox of each one of said X, Y and Z moving sections is coupled to a ball-screw mechanism via a screwed shaft respectively that rotates with the rotation of each one of said motor gear box, and wherein said ball-screw mechanism comprises a flange that moves along said screwed shaft that is attached to each one of said motor gearbox respectively when each one of said three motor gearbox rotates linearly displacing its respective said at least two wagons coupled to each one of respective said flange in X, Y and/or Z direction.

4. The robot traction provider system of claim 3, wherein a bottom side of said case and said flange of said Y moving section sits and is attached to a top side of said at least two chassis.

5. The robot traction provider system of claim 4, wherein said case and said flange of said X moving section sits and is fixedly attached to said case and said flange and at least two wagons of said Y moving section.

6. The robot traction provider system of claim 5, wherein said Z moving section, moves said traction provider robot up and down; and sits and is fixedly connected to said case and said flange and said at least two wagons of said X moving section; and wherein a foot holding shaft is fixedly attached to said Z moving section and its respective gear-box; therefore, allowing said traction provider robot and therefore said patient's foot to move in any desired direction as needed.

7. The robot traction provider system of claim 6, wherein said Z motor gearbox and Z moving section moves said ankle holder, sole holder and shin holder all together between 600 to 1100 millimeters and turns said patient's foot in a range of −90 up to +90 degrees in comparison with Z axis.

8. The robot traction provider system of claim 7, further comprising a pulse oximeter placed near said sole holder monitoring oxygen level of said patient.

9. The robot traction provider system of claim 8, wherein said system utilizes said three gearboxes and a fourth gearbox providing three linear and one rotational degrees of freedom respectively, therefore restoring said patient's foot in a desirable position, wherein said shaft is connected to said robot traction provider via said fourth gearbox wherein when said fourth gearbox turns said patient's foot will turn in XZ plane direction, consequently; wherein said three linear and rotational degrees of freedom have an accuracy of one millimeter and one degree respectively, wherein said robot traction provider system is a standalone system and independent with respect to an operating table, however it can be combined and attached to said operating table as needed.

* * * * *